(12) United States Patent
Fransson et al.

(10) Patent No.: US 10,179,162 B2
(45) Date of Patent: *Jan. 15, 2019

(54) CITRATE FREE PHARMACEUTICAL COMPOSITIONS COMPRISING ANAKINRA

(71) Applicant: Swedish Orphan Biovitrum AB (publ), Stockholm (SE)

(72) Inventors: Jonas Fransson, Uppsala (SE); Ebba Florin-Robertsson, Stockholm (SE)

(73) Assignee: SWEDISH ORPHAN BIOVITRUM AB (PUBL), Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,438

(22) Filed: Oct. 29, 2015

(65) Prior Publication Data
US 2016/0045568 A1 Feb. 18, 2016

Related U.S. Application Data

(63) Continuation of application No. 13/984,844, filed as application No. PCT/SE2012/050124 on Feb. 9, 2012, now Pat. No. 9,198,954.

(30) Foreign Application Priority Data

Feb. 11, 2011 (SE) ...................................... 1150109

(51) Int. Cl.
| | | |
|---|---|---|
| *A61K 38/20* | (2006.01) | |
| *C07K 14/545* | (2006.01) | |
| *C07K 14/715* | (2006.01) | |
| *A61K 38/17* | (2006.01) | |
| *A61K 9/00* | (2006.01) | |
| *A61K 47/26* | (2006.01) | |
| *A61K 9/10* | (2006.01) | |
| *A61K 47/02* | (2006.01) | |
| *A61K 47/18* | (2017.01) | |
| *A61K 38/00* | (2006.01) | |

(52) U.S. Cl.
CPC ........ *A61K 38/2006* (2013.01); *A61K 9/0019* (2013.01); *A61K 9/10* (2013.01); *A61K 38/1793* (2013.01); *A61K 47/02* (2013.01); *A61K 47/183* (2013.01); *A61K 47/26* (2013.01); *C07K 14/545* (2013.01); *C07K 14/7155* (2013.01); *A61K 38/00* (2013.01)

(58) Field of Classification Search
CPC ............ A61K 2300/00; A61K 38/1793; A61K 9/0019; A61K 38/00; A61K 38/2006; A61K 9/1623; C07K 14/7155
See application file for complete search history.

(56) References Cited

U.S. PATENT DOCUMENTS

| | | |
|---|---|---|
| 5,075,222 A | 12/1991 | Hannum et al. |
| 6,599,873 B1 | 7/2003 | Sommer et al. |
| 6,858,409 B1 | 2/2005 | Thompson et al. |
| 2007/0098684 A9 | 5/2007 | Raibekas et al. |

FOREIGN PATENT DOCUMENTS

| | | |
|---|---|---|
| CN | 101584857 | 11/2009 |
| WO | WO-94/06457 | 3/1994 |
| WO | WO-97/28828 | 8/1997 |
| WO | WO-2007/047969 | 4/2007 |
| WO | WO-2009/015345 | 1/2009 |

OTHER PUBLICATIONS

Bedele et al., "Cutaneous mast cell degranulation in rats receiving injections of recombinant human interleukin-1 receptor antagonist (rhIL-1ra) and/or its vehicle: Possible clinical implications," J Lab Clin Med (1995) 125:493-500.
Chang et al., "Physical factors affecting the storage stability of freeze-dried interleukin-1 receptor antagonist: glass transition and protein conformation," Arch Biochem Biophys (1996) 331(2):249-258.
English translation of CN101584857, downloaded from the European Patent Office on Apr. 18, 2014.
Extended European Search Report in EP12744410.7, dated Jun. 26, 2014, 6 pages.
Fransson et al., "Local tolerance of subcutaneous injections," J Pharm Pharmacal. (1996) 48:1012-1015.
Frenken et al., "Identification of the component part in an epoetin alfa preparation that causes pain after subcutaneous injection," Am J Kidney Dis. (1993) 22:553-556.
Gulliksson, et al. "Mast cell survival and mediator secretion in response to hypoxia," PLoS One (2010) 5(8):e12360.
Haller et al., "Safety Issues Specific to Clinical Development of Protein Therapeutics," Clin Pharmacal Ther. (2008) 84(5):624-627.
Hargreaves et al., "A new and sensitive method for measuring thermal nociception in cutaneous hyperalgesia," Pain (1988) 32:77-88.
International Preliminary Report on Patentability for PCT/SE2012/050124, dated May 15, 2013, 13 pages.
International Search Report and Written Opinion for PCT/SE2012/050124, dated Apr. 11, 2012, 12 pages.
Kanaan et al., "Endotoxin-induced local inflammation and hyperalgesia in rats and mice: a new model for inflammatory pain," Pain (1996) 66:373-379.
Laursen et al., "Pain Perception after Subcutaneous Injections of Media Containing Different Buffers," Basic & Clinical Pharmacology & Toxicology (2006) 98:218-221.
Nema et al., "Excipients: Parenteral Dosage Forms and Their Role," in Encyclopedia of Pharmaceutical Technology, Third Edition, Swarbrick, J. (ed.) (2006) vol. 3, pp. 1622-1644, Informa Healthcare, USA.

(Continued)

*Primary Examiner* — Robert S Landsman
*Assistant Examiner* — Bruce D. Hissong
(74) *Attorney, Agent, or Firm* — Morrison & Foerster LLP; Bu Yin

(57) ABSTRACT

The present invention relates to pharmaceutical compositions comprising anakinra as an active compound in the absence of sodium citrate. The said pharmaceutical compositions are useful for the treatment of IL-1 mediated disorders and for decreasing nociceptive pain during such treatment.

17 Claims, 4 Drawing Sheets

(56) References Cited

OTHER PUBLICATIONS

Piovezan et al., "Effects of endothelin-1 on capsaicin-induced nociception in mice," European Journal of Pharmacology (1998) 351:15-22.
Raibekas et al., "Anion Binding and Controlled Aggregation of Human Interleukin-1 Receptor Antagonist," Biochemistry (2005) 44:9871-9879.
Thaler et al., "Efficacy and safety of anakinra for the treatment of rheumatoid arthritis: an update of the Oregon Drug Effectiveness Review Project," Biologics (2009) 3:485-498.
Wang et al., "Review of excipients and pH's for parenteral products used in the United States," J. Parenter. Drug Assoc. (1980) 34:452-462.
Winder et al., "Acute effect of substance P and calcitonin gene-related peptide in human skin—A microdialysis study," J Invest Dermatol (2000) 115:1015-1020.
Yoshitake et al., "Determination of histamine in microdialysis samples from Guinea pig skin by high-performance liquid chromatography with fluorescence detection," Skin Pharmacol Physiol. (2012) 25(2):65-72.
Hauff et al., "Peptide-cased approaches to treat asthma, arthritis, other autoimmune diseases and pathologies of the central nervous system," Arch Immunol Ther Exp (2005) 53:308-320.
Office Action for RU 2013141548, dated Jan. 26, 2016, 6 pages. (Including English translation).
Restriction Requirement for U.S. Appl. No. 13/984,844, dated Dec. 4, 2013, 7 pages.
Response to Restriction Requirement for U.S. Appl. No. 13/984,844, dated Jan. 6, 2014, 6 pages.
Non-final Office Action for U.S. Appl. No. 13/984,844, dated May 6, 2014, 8 pages.
Response to Non-final Office Action for U.S. Appl. No. 13/984,844, dated Oct. 6, 2014, 26 pages.
Final Rejection for U.S. Appl. No. 13/984,844, dated Jan. 28, 2015, 9 pages.
Response to Final Rejection for U.S. Appl. No. 13/984,844, dated Mar. 27, 2015, 12 pages.
Advisory Action for U.S. Appl. No. 13/984,844, dated Apr. 13, 2015, 3 pages.
Notice of Appeal for U.S. Appl. No. 13/984,844, dated Jul. 28, 2015, 1 page.
Notice of Allowance for U.S. Appl. No. 13/984,844, dated Jul. 31, 2015, 13 pages.
First Examination Report for IN 7051/DELNP/2013, dated Jul. 18, 2018, 7 pages (Including English Translation).

CITRATE FREE PHARMACEUTICAL COMPOSITIONS COMPRISING ANAKINRA

CROSS-REFERENCE TO RELATED APPLICATIONS

This application is a continuation of U.S. patent application Ser. No. 13/984,844, filed Sep. 27, 2013, which is a national phase application of International Patent Application No. PCT/SE2012/050124 having an international filing date of Feb. 9, 2012, which claims priority to Sweden Patent Application No. 1150109-5 filed Feb. 11, 2011. The disclosures of the above-identified applications are herein incorporated by reference in their entireties for all purposes.

TECHNICAL FIELD

The present invention relates to pharmaceutical compositions comprising anakinra as an active compound in the absence of sodium citrate. The said pharmaceutical compositions are useful for the treatment of IL-1 mediated disorders and for decreasing nociceptive pain during such treatment.

BACKGROUND ART

Pharmaceutical formulations suitable for parenteral delivery typically comprise (a) an active molecule; (b) a buffering agent with sufficient buffering capacity to control solution pH; and (c) a tonicity agent to provide isotonicity of the formulation. Additionally, further components may be added such as antioxidants, specific stabilizers, surfactants, preservatives, etc., as needed depending on the specific active and its intended use.

The selection of the formulation components has to be based on thorough studies evaluating different components with respect to their function in the formulation and optimal stabilizing capacity. Furthermore, other formulation studies have to be performed to identify other solution parameters, such as optimal pH and ionic strength for the specific active molecule and its intended use. Studies are also performed to optimize the concentrations of the respective formulation components. In many cases, additional aspects of the final formulation and its clinical use have to be considered, such as appropriate injection volume, compatibility with physiological fluids or tissues, viscosity, local tolerance etc.

One example of local tolerance concerns the selection of buffer species. It is known that specific buffer species may provoke local in-tolerance or injection pain. Sodium citrate has been reported to cause pain upon subcutaneous injection in some cases (Frenken, 1993, Laursen, 2006). In addition, buffer concentration should be minimized to be optimal with respect to not only to pH stability in the drug formulation during long term storage, but also as having minimal impact on the physiological conditions at the injection site (e.g. Fransson and Espander-Jansson, 1996).

The list of components that can be added to a formulation for parenteral delivery is limited (Wang and Kowall, 1980; Nema, 2006). A number of aspects has to be considered; safety, prior experience in humans, availability from suppliers, etc. The stability of protein drugs in vivo and in vitro is a complex matter where multiple degradation reactions occur in parallel, such as oxidation, deamidation, aggregation etc. One major reaction occurring is formation of aggregates. Protein aggregates can form via covalent or non-covalent pathways, and can be of soluble or insoluble nature. The presence of protein aggregates is a major concern from safety perspective as it may impact the secondary and tertiary structure of the protein. Presence of specific non-native protein structures has been associated with increased immunogenicity of proteins potentially causing reduced efficacy or even in vivo immunological reactions to native proteins, with life threatening conditions as result.

Interleukin-1 mediated diseases include rheumatoid arthritis (RA), inflammatory bowel disease (IBD), sepsis, sepsis syndrome, osteoporosis, ischemic injury, graft vs. host disease, reperfusion injury, asthma, insulin diabetes, myelogenous and other leukemias, psoriasis and cachexia. These and other inflammatory diseases are characterized by the production of cytokines, including interleukin-1.

For those syndromes where a role for IL-1 in the pathology of the disease has been established, the clinical manifestations of the disease can rapidly be alleviated by treatment with anti-IL-1 medicines. One such medicine is Kineret®, whose active component, anakinra, is a recombinant version of the naturally occurring IL-1 receptor antagonist (IL-1ra). Anakinra is disclosed in, e.g. U.S. Pat. No. 5,075,222.

Kineret® (anakinra for injection) is formulated at 150 mg/ml with a 10 mM sodium citrate buffer (pH 6-7) and sodium chloride (140 mM) as tonicity agent. Furthermore, 0.5 mM EDTA and 0.1% (w/w) polysorbate 80 are used as stabilizers. The selection of sodium citrate as buffer component for anakinra was based on detailed studies evaluating the short and long term stability of anakinra at real time conditions. Several potential buffer components were evaluated, sodium phosphate being one and sodium citrate was identified as providing the optimal stability with respect to anakinra aggregation (Raibekas et al., 2005). Aggregation of anakinra was a major concern for the selection of the buffer component. The concentration of the sodium citrate was minimized as much as possible considering the local tolerability.

During clinical use of anakinra in 10 mM sodium citrate, it was found that the formulation caused issues with local tolerance at the subcutaneous injection site (Thaler, 2009). Injection site reactions are not uncommon with subcutaneous delivery of protein drugs and are a general problem (Haller, 2008) and are associated with clinical use of a large number of protein drugs. More than 50% of the patients using anakinra for injection experiences injection site reactions to some degree for the first injections. The nature and the mechanism of local reaction have been investigated and several conclusions have been made (Bendele, 1995). It has been concluded that the injection site reaction has multiple causes including anakinra molecule itself and the formulation components, sodium citrate having a very large impact.

Consequently, there is a need for anakinra compositions, suitable for injection, which are stable and which avoid the drawbacks with anakinra compositions comprising sodium citrate.

DISCLOSURE OF THE INVENTION

Figure 1:
FIG. 1 shows the number of sub-visible particles (larger than 5, 7.5 and 10 μm in size) per ml of various anakinra compositions (designated E, G, H, O, R, S, T, and U).

According to the invention, it has surprisingly been shown that anakinra, suitable for injection, can be sufficiently stabilized without the use of sodium citrate. In contrast to the findings by Raibekas et al. (2005), anakinra can be formulated in aqueous solution with an appropriate tonicity agent and additional stabilizers, but without sodium citrate as buffer. Under appropriate preparation conditions, anakinra will inherently control the solution pH. Even a solution with no added buffer may be sufficiently stable.

Consequently, in a first aspect the invention provides a pharmaceutical formulation comprising an effective amount of anakinra, wherein the said pharmaceutical formulation is in the absence of citrate.

Another aspect of the invention is method for the treatment or prevention of an IL-1 mediated disorder which comprises administering to a mammal, including man, in need of such treatment a pharmaceutical formulation comprising an effective amount of anakinra, wherein the said pharmaceutical formulation does not contain citrate.

According to the invention the said formulation is stable in the absence of citrate, wherein the term "stable" implies, for instance, that the absence of aggregation and/or pH stability is, at least, approximately equal to a similar anakinra formulation comprising 10 mM sodium citrate (pH 6-7).

The term "anakinra" means, in particular, the IL-1 receptor antagonist (IL-1ra) having the 152 amino acid sequence shown as positions 26-177 in NCBI Reference Sequence NP_776214.1. Further, the term "anakinra" should be understood as including modified forms of anakinra, e.g. amino acid variants having at least 90%, 95%, 97% or 99% identity with the anakinra amino acid sequence. The person skilled in the art will understand that many combinations of deletions, insertions, inversions and substitutions can be made within the anakinra amino acid sequence, provided that the resulting molecule ("the anakinra variant") is biologically active, e.g. possesses the ability to inhibit IL-1. Particular anakinra variants are described in e.g. U.S. Pat. Nos. 5,075,222; 6,858,409 and 6,599,873.

The term "anakinra" further includes fusion proteins comprising anakinra. Anakinra can be formatted to have a larger hydrodynamic size, for example, by attachment of a polyalkyleneglycol group (e.g. a polyethyleneglycol (PEG) group), serum albumin, transferrin, transferrin receptor or at least the transferrin-binding portion thereof, an antibody Fc region, or by conjugation to an antibody domain.

The term "an effective amount" refers to an amount that confers a therapeutic effect on the treated subject. The therapeutic effect may be objective (i.e. measurable by some test or marker) or subjective (i.e. the subject gives an indication of or feels an effect).

Preferably, anakinra is administered in a dose from 0.1 to 100 mg/kg per day, preferably 0.1 to 1 mg/kg per day. A preferred dosage for the treatment of IL-1 mediated diseases should produce blood anakinra concentrations between 1 and 1000 ng/ml. Accordingly, it is preferred that, initially, doses are administered to bring the circulating levels of anakinra above 5 ng per ml of plasma.

The pharmaceutical formulation according to the invention preferably comprises anakinra in an amount between 20 and 200 mg/ml, more preferably between 100 and 200 mg/ml, such as 150 mg/ml.

The pharmaceutical formulation according to the invention is preferably adapted for subcutaneous injection of anakinra. Preferably, the pharmaceutical formulation comprises a chelating agent, such as ethylenediaminetetraacetic acid (EDTA). The amount of EDTA in the formulation is preferably from 0.05 to 1 mM, more preferably around 0.5 mM. An emulsifier, preferably a non-ionic surfactant such as polysorbate 80 (also known as polyoxyethylene sorbitan monooleate or Tween 80™), can be added to the formulation to reduce aggregation and denaturation, as well as for increased solubility. The amount of polysorbate 80 is preferably between 0.01 and 1%, more preferably around 0.1%. Consequently, a preferred form of the pharmaceutical formulation according to the invention comprises 150 mg/ml anakinra, 0.5 mM EDTA and 0.1% polysorbate 80.

Further, the pharmaceutical formulation according to the invention can comprise a tonicity agent, e.g. NaCl, in an amount sufficient to provide isotonicity of the formulation. A preferred tonicity agent is NaCl in a concentration between 120 and 240 mM, preferably about 120-180 mM, such as about 120-150 mM, or most preferably around 140 mM.

Alternatively, the said tonicity agent can be a mixture of NaCl and a second tonicity agent selected from the group consisting of monosaccharides, disaccharides and sugar alcohols. Preferably, the second tonicity agent is selected from the group consisting of sucrose, mannitol, sorbitol, glycerol, inositol, and trehalose. More preferably, the second tonicity agent is mannitol, sorbitol or glycerol. Most preferably, the second tonicity agent is mannitol in an amount from 1 to 100 mg/ml, preferably from 5 to 50 mg/ml.

The invention includes pharmaceutical formulations wherein the active protein, i.e. anakinra, is sufficient as a buffering substance and capable of maintaining the pH at a desired level, preferably about pH 6.5. Consequently, no additional buffering substance has to be added to the formulation according to the invention. However, included in the invention are also pharmaceutical formulations comprising anakinra and at least one additional buffering substance, provided that the said additional buffering substance is not a citrate buffer. The said additional buffering substance can for instance be a phosphate buffer, or histidine. More specifically, the said additional buffer could be sodium phosphate in an amount of 1 to 50 mM, preferably around 10 mM, or histidine in an amount of 5 to 50 mM, preferably around 10 mM.

Particularly preferred formulations are those comprising a phosphate buffer in combination with mannitol. In such formulations, the concentration of phosphate, such as sodium phosphate, is preferably from 1 to 50 mM (more preferably around 10 mM) and the mannitol concentration is preferably from 5 to 50 mg/ml (more preferably around 10 mg/ml). The pH of the said formulation is preferably between 6 and 7, such as between 6.3 and 6.6, or more preferably around 6.5.

Consequently, preferred formulations according to the invention include formulations comprising:
- (a) anakinra (100-200 mg/ml):
- (b) EDTA (0.05-1 mM);
- (c) polysorbate 80 (0.01-1%);
- (d) NaCl (120-180 mM);
- (e) sodium phosphate, pH 6-7 (1-50 mM); and
- (d) mannitol (5-50 mg/ml).

A particularly preferred formulation comprises:
- (a) anakinra (150 mg/ml):
- (b) EDTA (0.5 mM);
- (c) Polysorbate 80 (0.1%);

(d) NaCl (120-150 mM, preferably 140 mM);
(e) sodium phosphate, pH 6.3-6.6, preferably pH 6.5 (10 mM); and
(d) mannitol (10 mg/ml).

The pharmaceutical formulation according to the invention can preferably be used in the treatment of at least one IL-1 mediated disorder. Included in the invention is also a method for the treatment of an IL-1 mediated disorder, comprising administering to a mammal, including humans, in need of such treatment a pharmaceutical formulation as defined herein. The term "treatment" includes prevention (prophylaxis) of IL-1 mediated disorders, or amelioration or elimination of the disorder once it has been established.

A disease or medical condition is considered to be an "IL-1 mediated disorder" if the spontaneous or experimental disease or medical condition is associated with elevated levels of IL-1 in bodily fluids or tissue or if cells or tissues taken from the body produce elevated levels of IL-1 in culture. In many cases, such interleukin-1 mediated diseases are also recognized by the following additional two conditions: (1) pathological findings associated with the disease or medical condition can be mimicked experimentally in animals by the administration of IL-1; and (2) the pathology induced in experimental animal models of the disease or medical condition can be inhibited or abolished by treatment with agents which inhibit the action of IL-1. In most interleukin-1 mediated diseases at least two of the three conditions are met, and in many interleukin-1 mediated diseases all three conditions are met.

IL-1 mediated disorders include:
Amyloid A amyloidosis
Adult onset Still's disease (AOSD)
Asthma
Behcet's disease
Blau syndrome
Cachexia
Calcium pyrophosphate dihydrate disease (CPPD)
Castleman's disease
Cryopyrin-associated periodic syndromes (CAPS)
Deficiency of the interleukin-1-receptor antagonist (DIRA)
Dermatomyositis
Erdheim-Chester's disease
Erosive osteoarthritis
Familial Mediterranean fever
Generalised pustular psoriasis
Gout and pseudogout
Graft vs. host disease
Hidradenitis Suppurativa
Hyper IgD syndrome (HIDS)
Idiopathic cold urticaria
Inclusion-body myositis
Inflammatory bowel disease (IBD)
Ischemic injury
Macrophage Activation Syndrome
Majeed syndrome
Mevalonate kinase deficiency
Myelogenous and other leukemias,
Neutrophilic panniculitis
Osteoporosis
Periodic fevers with aphthous stomatitis, pharyngitis, and adenitis (PFAPA)
Polymyositis
Psoriasis
Pyoderma gangrenosum, acne conglobata, and aseptic arthritis (PAPA)
Recurrent idiopathic pericarditis
Relapsing polychondritis
Reperfusion injury
Rheumatoid arthritis (RA)
Schnitzler's syndrome
Sepsis; sepsis syndrome
Smoldering myeloma
Synovitis Acne Pustulosis Hyperostosis Osteitis (SAPHO) syndrome
Systemic onset idiopathic juvenile arthritis (SoIJA)
Tumour necrosis factor receptor-associated periodic syndrome (TRAPS)
Type 1 diabetes
Type 2 diabetes
Urticarial vasculitis
Uveitis In a preferred form of the invention, the pharmaceutical formulation is administered by subcutaneous injection to a mammal, including humans, in need thereof. According to the invention, nociceptive pain at the site of subcutaneous injection is avoided or reduced. The term "nociceptive pain" implies neural activity initiated by nociceptors (pain receptors).

EXAMPLES

Example 1: Stability with Respect to Visible Aggregation

Frozen anakinra bulk solution in 10 mM sodium citrate, 140 mM NaCl and 0.5 mM EDTA, obtained from Amgen Manufacturing, was thawed and diafiltrated using a Millipore ProFlux™ M12 system, including a 0.1 $m^2$ Millipore Pellicon 2™ Mini cassette, having a 10 kDa composite regenerated cellulose PLC10 Membrane™ (Millipore). The obtained solutions were concentrated by Ultra filtration in according to standard methods.

The compositions described in Table I were prepared from the obtained diafiltered and concentrated solutions above. In addition to the ingredients shown in Table I, all compositions contained 150 mg/ml anakinra, 0.5 mM EDTA and 0.1% polysorbate 80. The solutions were filled in siliconized glass syringes (1 ml) which were stored for 1 month (+5° C. or +25° C.) or for 3 months (+5° C.).

TABLE I

Investigated anakinra compositions

| Composition | NaCl (mM) | Buffer (10 mM) | pH |
| --- | --- | --- | --- |
| E | 120 | Sodium citrate | 6.2 |
| G | 120 | Sodium phosphate | 6.2 |
| H | 120 | Histidine | 6.2 |
| O | 120 | — | 6.5 |
| R | 120 | Sodium citrate | 6.5 |
| S | 240 | Sodium citrate | 6.5 |
| T | 120 | Sodium phosphate | 6.5 |
| U | 120 | Sodium phosphate | 6.8 |

Figure 2:
FIG. 2 shows the number of particles as in FIG. 1, after the said anakinra compositions had been stored for 1 month at +25° C.
Figure 3:
FIG. 3 shows the number of particles as in FIG. 1, after the said anakinra compositions had been stored for 3 months at +5° C.

The solutions in Table I were tested for subvisible particles by a light blockage technique according to United States Pharmacopeia-National Formulary (USP-NF), Chapter 905, but adjusted to a small sample volume. At each time point samples from 3 syringes were pooled and tested. In each pool, the number of particles larger than 5, 7.5 and 10 μm in size was determined. The results are shown in Table II and FIGS. 1-3. Typical results for subvisible particles in parenteral products are in the range of less than 6000 particles larger than 10 μm.

TABLE II

Subvisible particles in anakinra formulations

| Composition | Start | 1 month +5° C. | 1 month +25° C. | 3 months +5° C. |
|---|---|---|---|---|
| | | Particles (>5 μm)/ml | | |
| E | 221 | 282 | 562 | 477 |
| G | 229 | 113 | 270 | 324 |
| H | 162 | 323 | 418 | 476 |
| O | 223 | 249 | 386 | 584 |
| R | 270 | 528 | 771 | 373 |
| S | 136 | 266 | 524 | 421 |
| T | 272 | 451 | 517 | 533 |
| U | 154 | 456 | 468 | 549 |

The measured amount of subvisible particles indicates that the visible aggregation of anakinra is relatively low, increases slightly over time, and is not dependent on presence of buffer. The data demonstrates that anakinra can be formulated without sodium citrate and with equivalent stability.

Example 2: Aggregation Stability

Anakinra compositions were prepared and stored as described in Example 1. The monomer content was measured by Size Exclusion Chromatography (SEC). Each sample was diluted with a 10 mM sodium citrate, 140 mM NaCl, 0.5 mM EDTA to an anakinra concentration of 5 mg/mL. The diluted sample was loaded on a TSK-Gel G2000 SWXL Column, 7.8 mm×30 cm (ToSoh Biosciences 08450) and eluted with a 10 mM sodium citrate, 140 mM NaCl and 0.5 mM EDTA at a flow of 0.5 mL/min. The absorbance at 280 nm was recorded and the % monomer was calculated from the respective peak area.

The results (Table III) show that the level of anakinra monomer remained stable for 3 months in all studied anakinra compositions.

TABLE III

Stability of various anakinra formulations

| Composition | Start | 1 month +5° C. | 1 month +25° C. | 3 months +5° C. |
|---|---|---|---|---|
| | | % monomer by SEC | | |
| E | 99.8 | 99.8 | 99.2 | 99.7 |
| G | 99.9 | 99.8 | 99.1 | 99.7 |
| H | 99.8 | 99.8 | 99.1 | 99.7 |
| O | 99.9 | 99.8 | 99.0 | 99.7 |
| R | 99.8 | 99.8 | 99.0 | 99.7 |
| S | 99.9 | 99.8 | 99.2 | 99.7 |
| T | 99.9 | 99.8 | 98.7 | 99.7 |
| U | 99.8 | 99.8 | 98.6 | 99.6 |

Example 3: pH Stability

Anakinra compositions were prepared and stored as described in Example 1. pH was measured according to standard procedures. The results (Table IV) show that pH remained stable for 3 months in all studied anakinra compositions.

TABLE IV pH stability of various anakinra formulations

| Composition | Start | 1 month +5° C. | 1 month +25° C. | 3 months +5° C. |
|---|---|---|---|---|
| | | pH | | |
| E | 6.1 | 6.1 | 6.1 | 6.1 |
| G | 6.1 | 6.0 | 6.0 | 6.1 |
| H | 6.1 | 6.1 | 6.1 | 6.2 |
| O | 6.1 | 6.0 | 6.0 | 6.1 |
| R | 6.2 | 6.2 | 6.2 | 6.2 |
| S | 6.1 | 6.0 | 6.0 | 6.1 |
| T | 6.4 | 6.4 | 6.4 | 6.5 |
| U | 6.7 | 6.7 | 6.7 | 6.7 |

Example 4: Stability of Anakinra Compositions Comprising Phosphate and Mannitol

Frozen anakinra bulk solution in 10 mM sodium citrate, 140 mM NaCl and 0.5 mM EDTA, obtained in-house, was thawed and diafiltrated using a Millipore ProFlux™ M12 system, including a 0.1 m² Millipore Pellicon 2™ Mini cassette, having a 10 kDa composite regenerated cellulose PLC10 Membrane™ (Millipore). The obtained solutions were concentrated by Ultra filtration in according to standard methods.

The compositions described in Table V were prepared from the obtained diafiltered and concentrated solutions above. In addition to the ingredients shown in Table V, all compositions contained 150 mg/ml anakinra. The solutions were filled in siliconized glass syringes (1 ml) which were stored at different temperatures to test the stability of anakinra in these formulations. The samples were stored for 1 month at +30° C., 2 and 4 months at +25° C.

TABLE V

Investigated anakinra compositions

| Composition | NaCl (mM) | Buffer | Mannitol | Polysorbate 80 | EDTA | pH |
|---|---|---|---|---|---|---|
| A | 145 | 10 mM Sodium citrate | 0 | (0.1%) | 0.5 mM | 6.3 |
| C | 145 | 10 mM Sodium phosphate | 10 mg/mL | (0.1%) | 0.5 mM | 6.3 |
| D | 145 | 10 mM Sodium phosphate | 0 | (0.1%) | 0.5 mM | 6.3 |
| D2 | 145 | 10 mM Sodium phosphate | 10 mg/mL | (0.01%) | 0.1 mM | 6.3 |

The monomer content was measured by Size Exclusion Chromatography (SEC) after storage at each temperature. Each sample was diluted with a 10 mM sodium citrate, 140 mM NaCl, 0.5 mM EDTA to an anakinra concentration of 5 mg/mL. The diluted sample was loaded on a TSK-Gel G2000 SWXL Column, 7.8 mm×30 cm (ToSoh Biosciences 08450) and eluted with a 10 mM sodium citrate, 140 mM NaCl and 0.5 mM EDTA at a flow of 0.5 mL/min. The absorbance at 280 nm was recorded and the % monomer was calculated from the respective peak area. The results of the Size Exclusion Chromatography (SEC) analysis presented in Table VI show that the level of anakinra monomer remained stable for up to 4 months in all studied anakinra compositions.

TABLE VI

Stability of the investigated anakinra formulations

| Composition | Start | 1 month +30° C. | 2 months +25° C. | 4 months +25° C. |
|---|---|---|---|---|
| | | % monomer by SEC | | |
| A | 99.8 | 95.3 | 96.8 | 92.9 |
| C | 99.8 | 95.5 | 96.9 | 93.1 |
| D | 99.8 | 95.0 | 96.6 | 92.3 |
| D2 | 99.8 | 95.7 | 97.0 | 93.2 |

Furthermore, proteins such as anakinra are typically sensitive to changes in pH. To evaluate any effect of pH on anakinra in the performed studies were the pH values in the formulations recorded. The results are shown in Table VII and show an increase in pH over time but this change is independent of formulation and the exhibited differences in monomer content in Table VI is not caused by a difference in pH.

TABLE VII

Solution pH of the investigated anakinra formulations

| Composition | Start | 1 month +30° C. | 2 months +25° C. | 6 months +5° C. |
|---|---|---|---|---|
| | | pH | | |
| A | 6.3 | 6.3 | 6.5 | 6.5 |
| C | 6.3 | 6.3 | 6.5 | 6.4 |
| D | 6.3 | 6.3 | 6.5 | 6.5 |
| D2 | 6.3 | 6.3 | 6.5 | 6.5 |

Example 5: Effect of Anakinra Compositions in Hargreaves Test

The aim of these studies was to compare the effect of different formulations of anakinra (citrate buffer or phosphate/mannitol buffer) on thermal nociception threshold and hind paw volume in male Sprague-Dawley rats (Hargreaves et al, 1988).

Figure 4:
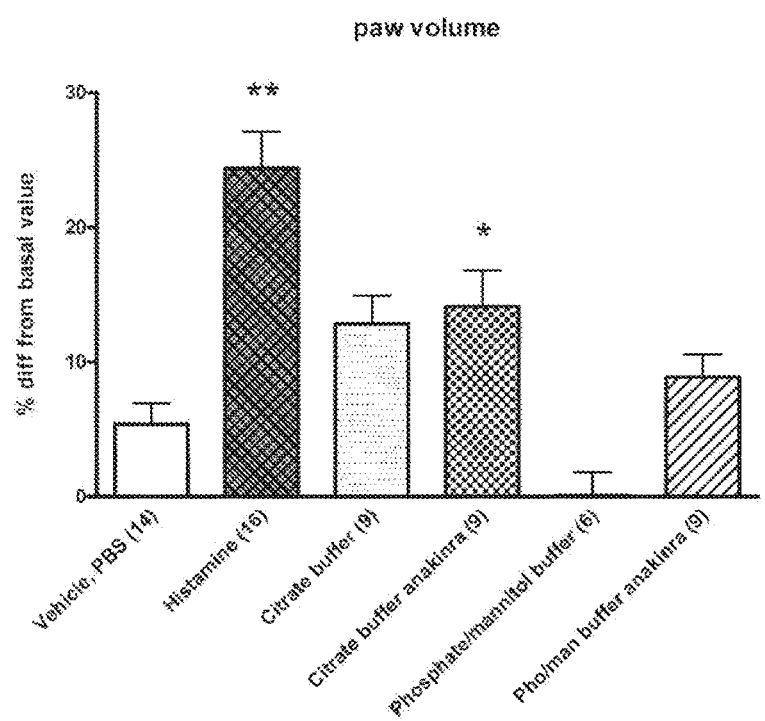
FIG. 4 indicates inflammation, as indicated by increased paw volume, in male Sprague-Dawley rats after administration of various anakinra compositions.

Intraplantar administration of histamine (50 μl/paw, 3 mg/ml), citrate buffer (10 mM pH 6.3) or phosphate buffer (10 mM, pH 6.3, plus mannitol 10 mg/ml) with or without anakinra (150 mg/ml), was made in the in right hind paw. Oedema formation, measured as an increase in paw volume after 2 hours indicated that citrate buffer and citrate buffered anakinra as well as phosphate/mannitol buffered anakinra caused acute inflammation (FIG. 4). Phosphate/mannitol buffer did not cause acute inflammation. Histamine (0.15 mg/paw), used as a positive control, induced thermal hyperalgesia and oedema formation.

In conclusion, there was a clear difference in paw swelling after 2 h between citrate buffer and phosphate/mannitol buffer alone. Additionally, paw volume measurements 2 h after injection showed a tendency for phosphate/mannitol-buffered anakinra to cause less oedema formation compared to citrate-buffered anakinra

Example 6: Effect of Anakinra Compositions on Evans Blue Permeability in Rats Male rats are anaesthetized with isoflurane, and the fur on the back and sides is carefully shaved away with clippers, carefully avoiding traumatization. A grid with 8 squares is drawn on the exposed skin on the back and sides with a marking pen. Evans Blue solution (1 mg/kg; Sigma-Aldrich) is administered by injection into the lateral tail vein, prior to subcutaneous injection of anakinra test solutions (1000 μl) in a random pattern within the grid squares. After the injection, the animals are returned into their cages and allowed to recover from anaesthesia. 6 hours after injection, the animals are euthanized by exposure to carbon dioxide. The skin is removed from the back and cleaned from adipose and connective tissue, and mounted on a board with the furry side down. The size of the zone of extravased Evans Blue dye in millimeters is measured by a centimeter ruler, and a subjective score ranging from 0 to 4 is assigned to the extravasation reaction, based on the intensity of dye staining.

Various anakinra compositions, including anakinra in "CSEP" (10 mM sodium citrate; 0.5 mM EDTA, 0.1% polysorbate 80, and 140 mM NaCl, pH 6.5), as well as phosphate buffered saline (PBS) as a control, are administered. The measured permeability changes indicate that injection of 1 ml PBS alone results in only minor leakage of Evans Blue dye from the site of injection. In contrast, injection of anakinra, dissolved at 100 mg/ml in CSEP, strongly increases permeability.

Example 7: Effect of Anakinra Compositions on Mouse Nociceptive Behavior

In order to assess the algesiogenic action of different anakinra compositions at the site of injection, the mouse hind paw licking model (Piovezan et al., 1998) is used. The animals are placed individually in chambers (transparent glass cylinders) and are acclimatized for at least 20 min before sub-plantar injection of various test anakinra compositions, including anakinra in CSEP (see Example 6) as well as PBS as a control. After challenge, the mice are observed individually for 15-30 min. The amount of time spent licking the injected paw is measured with a stop watch and is considered as indicative of nociceptive behavior.

Example 8: Effect of Anakinra Compositions in Hot Plate Test

In order to assess the algesiogenic actions of different anakinra compositions at the site of injection, the mouse thermal hyperalgesia model (Kanaan et al., 1996) is used. Animals are acclimatized to a hot plate instrument (Ugo Basil, Italy), preheated to 30° C., 1-2 days before testing. On the day of testing, animals receive sub-plantar injection of various test anakinra compositions, including anakinra in CSEP (see Example 6) as well as PBS as a control. With the experimenter blind to the treatment, mice are tested on the hot plate set to +52° C. Response latency is determined as the time taken to lick a hind paw or jump.

Example 9: Effect of Different Anakinra Formulations on Mast Cell Degranulation, In Vitro A23187 (a calcium ionophore) and dose-response IgE-anti-IgE serve as positive controls for mast cell activation. Mast cells from 10 different individuals (5 from cord blood and 5 from adult individuals) are isolated. The mast cells are isolated through CD34-selection (flow cytometry) of hematopoietic cells, which are subsequently grown at 37° C., 5% $CO_2$ under serum-deprived conditions, in the presence of human recombinant stem cell factor (Stemgen®) and IL-6 during 6-8 weeks (Gulliksson, M. et al., 2010). The degree of mast cell degranulation, after subjecting the cells to the different anakinra formulations, is assessed through measurements of histamine and PGD2. A change in mast cell degranulation is a measure of an alteration in the activation levels of the mast cells, which is a marker for the mechanisms of the acute inflammatory pain.

Example 10: Effect of Subcutaneous Anakinra Compositions on Extracellular Pain Mediators Release at the Site of Injection Using Microdialysis Method To investigate the acute effect of injection of various anakinra compositions including anakinra in CSEP (see Example 6) as well as PBS as a control, a well known microdialysis method for determination of extracellular concentrations of biochemical pain mediators (e.g. neurotransmitters, neuromodulators, and acute inflammatory cytokine and chemokine) is used. Animals are anaesthetized by inhalation of isoflourane during the experiment. The microdialysis probe is inserted into the dermis of the skin at the upper neck of each animal. The inlet tubing of the microdialysis probe is connected to a microinfusion pump and a Krebs-Ringer solution is be pumped at a flow rate of 1-10 ml/min. The samples are collected and the pain mediator is analyzed (e.g. by ELISA) for each individual experiment (Weidner C., et al., 2000 and Yoshitake T. et al., 2012).

REFERENCES

Bedele A., Colloton M., Vrkljan M., Morris J and Sabados K. (1995): Cutaneous mast cell degranulation in rats receiving injections of recombinant human interleukin-1 receptor antagonist (rhIL-1ra) and/or its vehicle: Possible clinical implications. *J. Lab. Clin. Med.* 125: 493-500.

Fransson J. and Espander-Jansson A. (1996): Local tolerance of subcutaneous injections. *J. Pharm. Pharmacol.* 48: 1012-1015.

Frenken, L. A., van Lier, H. J., Jordans, J. G., Leunissen, K. M., van Leusen, R., Verstappen, V. M., Koene, R. A. (1993): Identification of the component part in an epoetin alfa preparation that causes pain after subcutaneous injection. *Am. J. Kidney Dis.* 22: 553-556.

Gulliksson, M. et al. (2010) Mast cell survival and mediator secretion in response to hypoxia. *PLoS One* 5(8):e12360.

Haller C., Cosenza M. and Sullivan J. (2008): Safety Issues Specific to Clinical Development of Protein Therapeutics. *Clin Pharmacol Ther.* 84(5): 624-627.

Hargreaves K. et al. (1988): A new and sensitive method for measuring thermal nociception in cutaneous hyperalgesia. *Pain* 32: 77-88.

Kanaan S. A. et al: (1996): Endotoxin-induced local inflammation and hyperalgesia in rats and mice: a new model for inflammatory pain. *Pain* 66: 373-379.

Laursen T., Hansen B and Fisker S. (2006): Pain Perception after Subcutaneous Injections of Media Containing Different Buffers. *Basic & Clinical Pharmacology & Toxicology* 98: 218-221.

Nema S., Brendel R. and Washkuhn R.: Excipients: Parenteral Dosage Forms and Their Role. In: Swarbrick, J. (Ed.) *Encyclopedia of Pharmaceutical Technology*, third edition. Informa Healthcare, 2006.

Piovezan A. P. et al. (1998): Effects of endothelin-1 on capsaicin-induced nociception in mice. *European Journal of Pharmacology* 351: 15-22

Raibekas A, Bures E., Siska C., Kohno T., Latypov R. and Kerwin B. (2005): Anion Binding and Controlled Aggregation of Human Interleukin-1 Receptor Antagonist. *Biochemistry* 44: 9871-9879.

Thaler K., Chandiramani D., Hansen R., and Gartlehner G. (2009): Efficacy and safety of anakinra for the treatment of rheumatoid arthritis: an update of the Oregon Drug Effectiveness Review Project. *Biologics* 3: 485-498.

Wang J., Kowall R. (1980): Review of excipients and pH's for parenteral products used in the United States. *Journal of Parenteral Drugs* 34: 452-462.

Winder C., et al. (2000): Acute effect of substance P and calcitonin gene-related peptide in human skin—A microdialysis study. *The Journal of Investigative Dermatology.* 115: 1015-1020.

Yoshitake T., et al. (2012): Determination of histamine in microdialysis samples from Guinea pig skin by high-performance liquid chromatography with fluorescence detection. *Skin Pharmacology Physiology* 25:65-72.

The invention claimed is:

1. A pharmaceutical composition for injection, comprising:
   (a) anakinra in an amount between 20 mg/ml and 200 mg/ml, and
   (b) mannitol in an amount from 5 mg/ml to 50 mg/ml, wherein the pharmaceutical composition is free of citrate, and wherein the pharmaceutical composition is suitable for injection in a subject in need thereof.

2. The pharmaceutical composition of claim 1, which is adapted for subcutaneous injection.

3. The pharmaceutical composition of claim 1, further comprising a chelating agent.

4. The pharmaceutical composition of claim 3, wherein the chelating agent is EDTA in an amount from 0.05 mM to 1 mM.

5. The pharmaceutical composition of claim 1, further comprising an emulsifier.

6. The pharmaceutical composition of claim 5, wherein the emulsifier is the non-ionic surfactant polysorbate 80 in an amount from 0.01% to 1% (w/w).

7. The pharmaceutical composition of claim 1, comprising 150 mg/ml anakinra, 0.5 mM EDTA, and 0.1% (w/w) polysorbate 80.

8. The pharmaceutical composition of claim 1, further comprising a tonicity agent in an amount sufficient to provide isotonicity of the composition.

9. The pharmaceutical composition of claim 8, wherein the tonicity agent is NaCl in an amount from 120 mM to 240 mM.

10. The pharmaceutical composition of claim 8, wherein the tonicity agent is a mixture of NaCl and a second tonicity agent selected from the group consisting of a monosaccharide, a disaccharide, and a sugar alcohol.

11. The pharmaceutical composition of claim 1, comprising at least one additional buffering substance.

12. The pharmaceutical composition of claim 11, wherein the additional buffering substance is phosphate in an amount from 1 mM to 50 mM.

13. The pharmaceutical composition of claim 12, comprising 10 mM phosphate and 10 mg/ml mannitol.

14. A method for treating an IL-1 mediated disorder, comprising administering, to a subject in which such treatment is needed or desirable, an effective amount the composition of claim 1, whereby the IL-1 mediated disorder is treated.

15. The method of claim 14, wherein the IL-1 mediated disorder is rheumatoid arthritis.

16. The method of claim 14, wherein the composition is administered via subcutaneous injection.

17. The method of claim 16, wherein nociceptive pain at the site of subcutaneous injection is reduced.

* * * * *